US012616565B2

(12) United States Patent
Micheletti et al.

(10) Patent No.: US 12,616,565 B2
(45) Date of Patent: May 5, 2026

(54) PINHOLE INTRAOCULAR ONLAY

(71) Applicants: John Morgan Micheletti, Sugar Land, TX (US); Erin Andrew Doe, Katy, TX (US)

(72) Inventors: John Morgan Micheletti, Sugar Land, TX (US); Erin Andrew Doe, Katy, TX (US)

(73) Assignee: Ophthalmic Neo-Innovations of Texas, LLC, Sugar Land, TX (US)

( * ) Notice: Subject to any disclaimer, the term of this patent is extended or adjusted under 35 U.S.C. 154(b) by 577 days.

(21) Appl. No.: 18/162,230

(22) Filed: Jan. 31, 2023

(65) Prior Publication Data

US 2023/0240834 A1     Aug. 3, 2023

Related U.S. Application Data

(60) Provisional application No. 63/305,637, filed on Feb. 1, 2022.

(51) Int. Cl.
*A61F 2/16* (2006.01)
*A61F 2/14* (2006.01)
*B29D 11/02* (2006.01)

(52) U.S. Cl.
CPC .............. *A61F 2/1613* (2013.01); *A61F 2/15* (2015.04); *A61F 2002/16901* (2015.04); *B29D 11/026* (2013.01)

(58) Field of Classification Search
CPC .................................. A61F 2/15; B29D 11/026
See application file for complete search history.

(56) References Cited

U.S. PATENT DOCUMENTS

| | | | |
|---|---|---|---|
| 4,955,904 | A | 9/1990 | Atebara et al. |
| 5,245,367 | A | 9/1993 | Miller et al. |
| 5,980,040 | A | 11/1999 | Xu et al. |
| 10,299,912 | B2 | 5/2019 | Grant |
| 11,464,625 | B2 | 10/2022 | Link et al. |
| 2012/0271412 | A1 | 10/2012 | Feingold et al. |
| 2013/0131795 | A1 | 5/2013 | Miller et al. |
| 2016/0081791 | A1 | 3/2016 | Cady |
| 2017/0144392 | A1 | 5/2017 | Reboul et al. |
| 2017/0304045 | A1 | 10/2017 | Cady |
| 2019/0254808 | A1 | 8/2019 | Cady |
| 2021/0282920 | A1 | 9/2021 | Cady |

FOREIGN PATENT DOCUMENTS

| | | | | |
|---|---|---|---|---|
| EP | 2823789 | A1 | 1/2015 | |
| GB | 2458495 | A | 9/2009 | |
| WO | WO-2020107127 | A1 * | 6/2020 | ........... H04N 13/106 |
| WO | WO-2020201588 | A1 * | 10/2020 | ............. A61F 2/161 |
| WO | 2021141557 | A2 | 7/2021 | |

* cited by examiner

*Primary Examiner* — Javier G Blanco
(74) *Attorney, Agent, or Firm* — Henry L. Ehrlich

(57) ABSTRACT

An intraocular onlay includes a body with an optic portion and feet, the optic portion includes an anterior surface and a posterior surface, an annular mask of a selected optical opacity forming a pinhole, and a second optically transparent region exterior to the annular mask, where the feet extend from optic portion to be positioned within a capsular bag and rest on top of an existing intraocular lens that is located in the capsular bag.

9 Claims, 5 Drawing Sheets

PINHOLE INTRAOCULAR ONLAY

TECHNICAL FIELD

This disclosure relates in general to the field of ophthalmic lenses, and more particularly, but not by way of limitation, to an onlay for positioning on an intraocular lens to address pseudophakic presbyopia.

BACKGROUND

This section provides background information to facilitate a better understanding of the various aspects of the disclosure. It should be understood that the statements in this section of this document are to be read in this light, and not as admissions of prior art.

Cataract surgery is the most commonly performed surgery in the United States and results with removal of a cataract and implantation of an intraocular lens (IOL). Nearly 3-4 million people a year have cataract surgery every year and this number continues to grow. Once a patient has undergone surgery to remove and replace the cataract with an IOL, they may be left with pseudophakic presbyopia, which is the inability to see up close (near vision) following surgery. Nearly 80% of cataract surgery patients experience this condition. Some patients elect to have an extended depth of focus or multifocal IOL implanted at the time of surgery, but this is an extra expense not covered by insurance and remains a lesser percentage of the total. As it stands now, this is currently the only time the patient has a choice for a presbyopia correcting lens. Once cataract surgery has been performed on both eyes, which usually occurs within two weeks of the first surgery, the window for implantation of an IOL that corrects presbyopia has closed, unless a riskier procedure called an IOL exchange is performed.

Many patients that had cataract surgery without a presbyopia correcting IOL later desire to be independent of, or less dependent on, glasses, but this may occur years after cataract surgery. Patients may have more financial resources available at this time than they did at the time of cataract surgery, which prevented those patients from a presbyopia correcting IOL. They also may not have understood what life with a monofocal IOL would entail. Furthermore, their hobbies or interests or occupations may have changed and now more near vision is required for activities of daily life or enjoyment and employment.

Currently, there are no FDA approved, non-sulcus, permanent surgical options for pseudophakic patients to improve their near vision without compromising distance vision (as is the case with refractive corneal surgeries). The pinhole intraocular onlay enables pseudophakic patients to have an ultra-thin, new generation, novel intraocular onlay to be placed on top of the existing intraocular lens within the capsular bag and treat presbyopia.

SUMMARY

An exemplary pinhole intraocular onlay includes a body with an optic portion and feet, the optic portion includes an anterior surface and a posterior surface, an annular mask of a selected optical opacity forming a pinhole, and a second optically transparent region exterior to the annular mask, where the feet extend from the optic portion to be positioned within a capsular bag and rest on top of an existing intraocular lens that is located in the capsular bag.

An apparatus for addressing pseudophakic presbyopia including an intraocular lens (IOL) having a lens portion and haptics positioned in a capsular bag of an eye and an onlay having feet and an optic portion, the optic portion including an anterior surface and a posterior surface, an annular mask of a selected optical opacity forming a pinhole, and a second optically transparent region exterior to the annular mask, wherein the feet are positioned on top of the IOL and under a capsulorhexis edge of the capsular bag with the pinhole aligned on a visual axis of the eye.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion. As will be understood by those skilled in the art with the benefit of this disclosure, elements and arrangements of the various figures can be used together and in configurations not specifically illustrated without departing from the scope of this disclosure.

DETAILED DESCRIPTION

Figure 1:
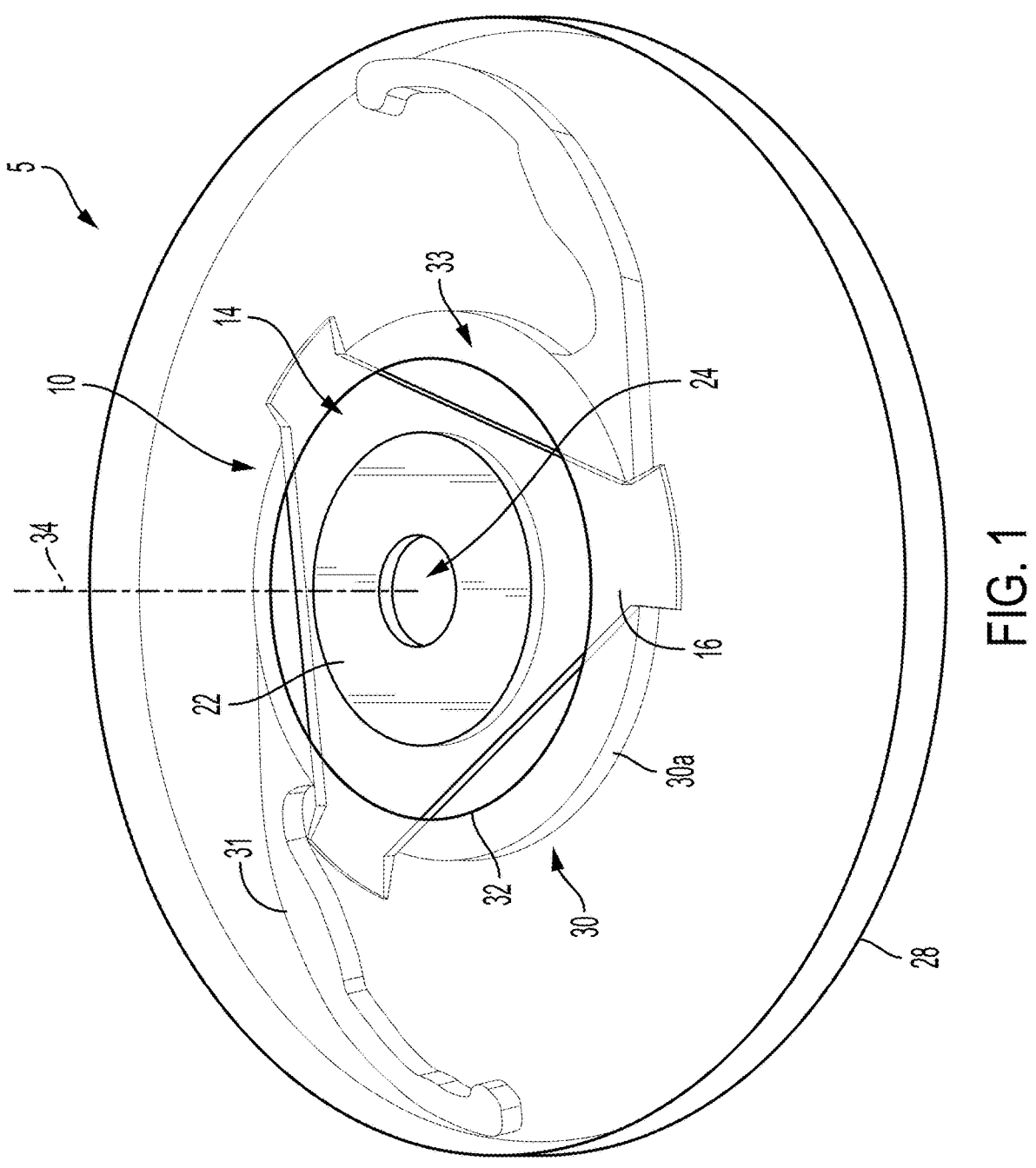
FIG. 1 is a perspective view of an intraocular lens disposed in a capsular bag of an eye and an exemplary pinhole intraocular onlay located on top of the intraocular lens with feet tucked under the capsularhexis edge.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

The pinhole intraocular onlay is an advanced technology IOL that is implanted on top of an existing IOL within the capsular bag. This novel design does not have outright haptics, but footplates that are tucked into the capsular bag between the optics of the pinhole intraocular onlay and the existing IOL. The power and optics of the intraocular onlay can be varied and in an embodiment is designed to utilize a pinhole. The plano (no power) intraocular onlay rests on top of the existing IOL within the capsular bag and is less likely to be prone to the issues of sulcus fixated or other piggyback IOLs, such as glaucoma, endothelial loss, transillumination iris defects, or inter-lenticular membranes due to not contacting any vascularized tissue.

A central opening in the intraocular onlay may be left without any material (a punched area centrally), a true pinhole effect, or may be filled with a refractive material. In some embodiments there is an offset of the footplates to the optical area, which decreases contact between the existing IOL and the intraocular onlay to minimize or prevent an inter-lenticular membrane. While a membrane might occur outside the area of the intraocular onlay, it would be rare for a new membrane to grow over intraocular devices.

The intraocular onlay is an intraocular lens that functions as a new class of IOL with footplates that rest within the capsular bag and on top of an existing IOL. The intraocular onlay has presbyopia correction via strategy of modifying, filtering, or focusing light which may include a pinhole, diffractive optics, accommodative optics, or prismatic optics. The intraocular onlay comprises flexible materials that are biocompatible which may include a hydrophobic or hydrophilic acrylic, a collagen copolymer (e.g., COL-LAMER (STAAR Surgical, Monrovia, CA)), silicone, or another flexible polymer, copolymer, or monomer.

In some embodiments, the central opening is a true opening, not just an optically clear opening but an actual hole, for the purposes of both the pinhole optic and prevention of a visually significant inter-lenticular membrane. The central opening may be left without any material (a void, a centrally punched area), a true pinhole effect, or may be filled with a refractive material.

In another embodiment, the intraocular onlay is embedded with a sensor or multiple sensors or other electronic devices that can measure and transmit biologic data such as glucose, intraocular pressure, or other biometric measurements. This may include radio-frequency identification tags, Bluetooth, near field communication, or other transmitting strategies for the purpose of storing and/or transmitting information from the intraocular onlay to an external transmitting or receiving device, such as, but not limited to, a smartphone. In another embodiment, the intraocular onlay can be fitted with a display device to provide augmented reality or a heads-up display to the patient in whom it is implanted.

FIGS. 1-7 illustrate exemplary aspects of a pinhole intraocular onlay 10. Intraocular onlay 10 has a body 12 having an optic portion 14 and feet 16. Body 12 may be constructed of an optically transparent material. Optic portion 14 includes an anterior surface 18 and a posterior surface 20, an annular mask 22 of a selected optical opacity forming a pinhole 24, and a second, optically transparent, region 26 exterior to annular mask 22. Feet 16 extend from second region 26. Feet 16 may extend from second region 26 in the sense that feet 16 are an outer portion of the exterior region. Anterior and posterior are used with reference to placement of the onlay relative to an eye. The posterior surface is positioned adjacent to the existing IOL and facing the eye and the anterior surface is facing outward from the eye and the existing IOL.

Annular mask 22 extends from an inner edge 22a defining pinhole 24 to an outer edge 22b. Annular mask 22 may be formed with a pigment embedded in the body or a separate disk mated with the body. The thickness of annular mask 22 may range from a few microns to the full thickness of optic portion 14. Pinhole 24 is generally 1.0 to 4.0 mm and in some embodiments in the range of about 1.0 to 2.0 mm. Annular mask 22 functions with the human pupil and generally has a width of about 0.75 to 1.0 mm. The dimensions of pinhole 24 and annular mask 22 may be fitted to the particular patient's eye. Pinhole 24 may comprise the optically clear body material without a refractive power or pinhole 24 may be an empty void extending the depth of onlay 10 through anterior surface 18 and posterior surface 20.

Figure 2:
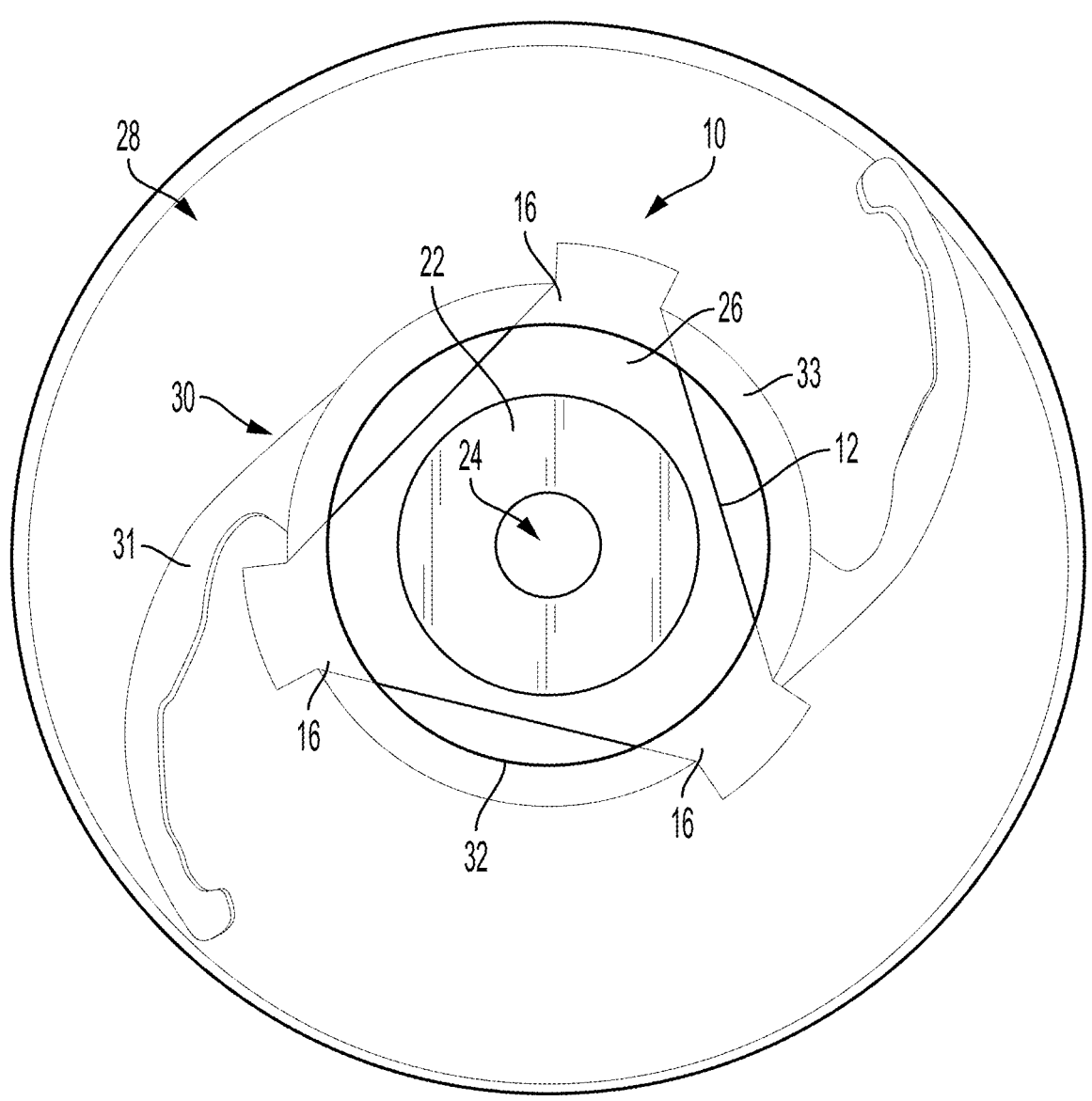
FIG. 2 is a top view of an exemplary pinhole intraocular onlay located on top of the intraocular lens with feet tucked under the capsularhexis edge.

In use, as illustrated for example in FIGS. 1-2, an intraocular lens (IOL) 30, having a haptics 31 extending radially outward from a periphery 30a of the lens portion 33, is positioned in a capsular bag 28 of a patient's eye 5. IOL 30 was implanted in a procedure prior to placement of onlay 10 and the patient has pseudophakic presbyopia. Onlay 10 is manipulated to position feet 16 within capsular bag 28 and resting on top of IOL 30. Feet 16 are tucked under the capsularhexis edge 32 and there is no need to expose the periphery 30a of IOL 30 to implant onlay 10. Onlay 10 can be folded, rolled, or injected into the anterior camber through a very small incision. This is critical in that it is often very difficult to expose the IOL edge years after the IOL was implanted.

Onlay 10 is not rigid and is not clipped onto IOL 30 and it can therefore be centered on the visual axis 34 (pinhole 24 centered on the visual axis) regardless of the position of the existing IOL 30. It is common for IOLs to decenter during the first year after implantation. Unless a very good capsularhexis is created during the original surgery and unless the opening is perfectly centered around the original IOL, it is probable that IOL 30 is not perfectly aligned with visual axis 34. It normally does not matter if the IOL is centered on the visual axis because IOLs have equal refractive powers throughout. However, to utilize a pinhole effect the pinhole must be centered on the visual axis. Not requiring the onlay be clipped to IOL 30 allows for the onlay to be centered on the visual axis as well as not requiring that the IOL periphery be exposed to implant onlay 10.

Figure 3:
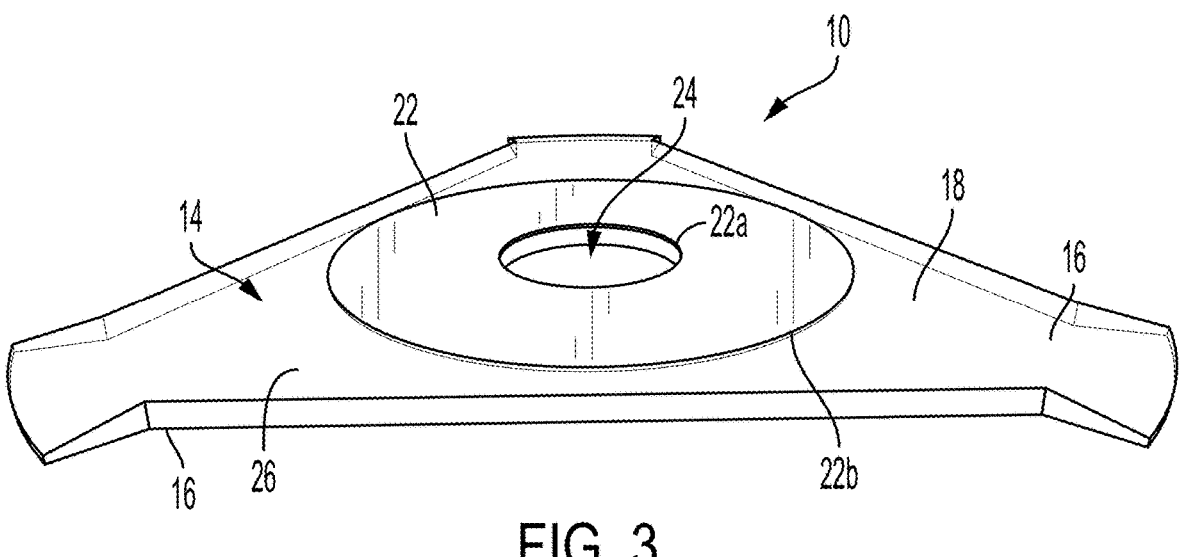
FIG. 3 is a top perspective view of an exemplary pinhole intraocular onlay.
Figure 4:
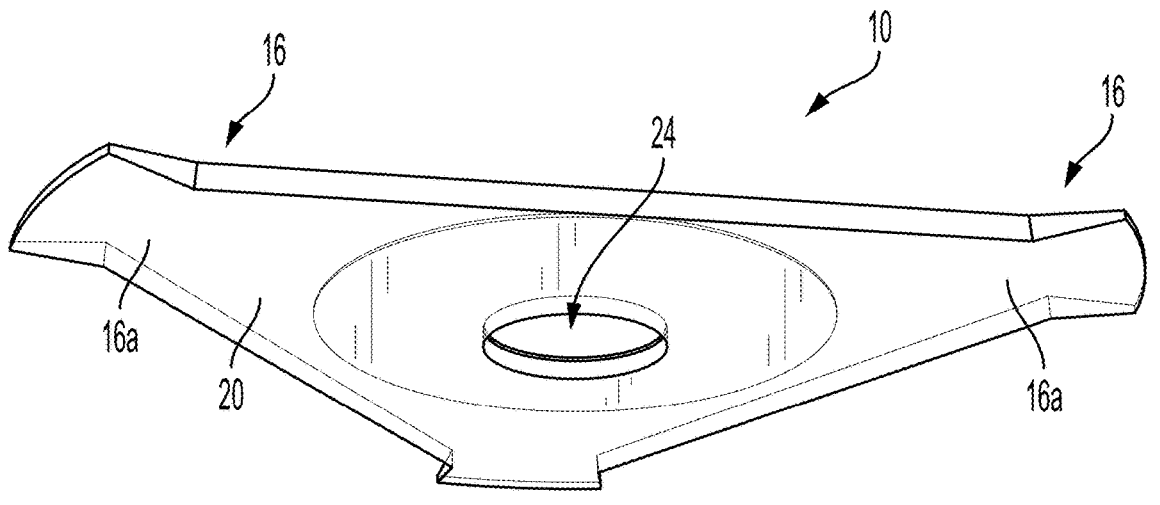
FIG. 4 is a bottom perspective view of the exemplary pinhole intraocular onlay of FIG. 3.
Figure 6:
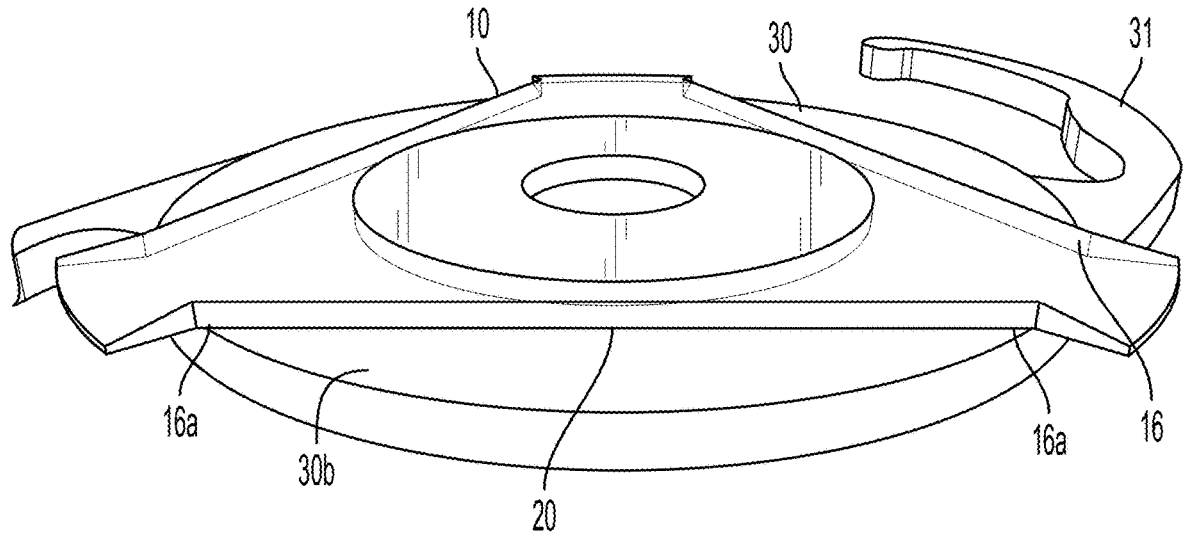
FIG. 6 is a perspective view of an exemplary pinhole intraocular onlay positioned on top of an intraocular lens.
Figure 7:
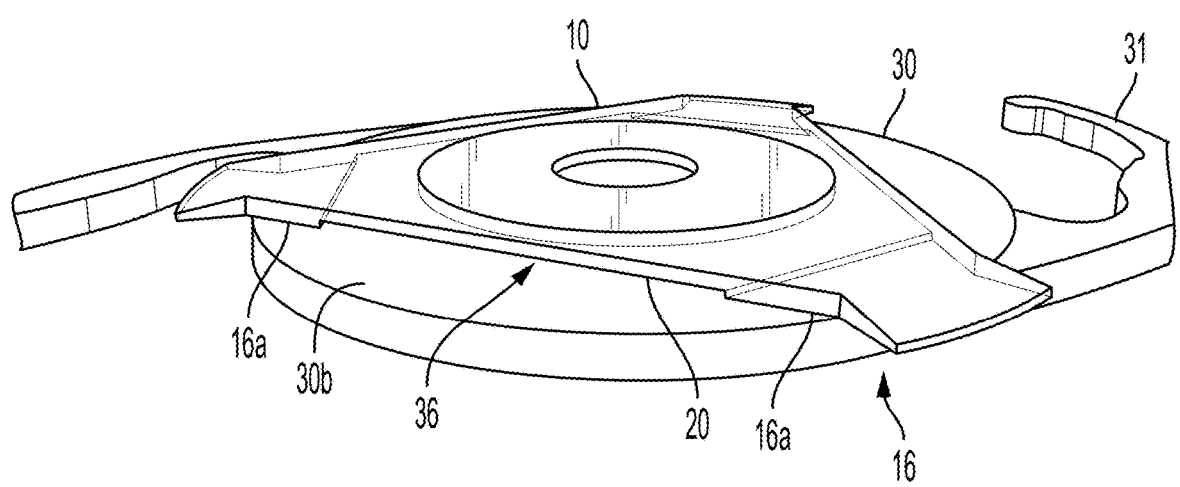
FIG. 7 is a perspective view of an exemplary pinhole intraocular onlay positioned on top of an intraocular lens with an open gap between an optic portion of the onlay and the intraocular lens.

FIGS. 6 and 7 illustrate exemplary onlays 10 with feet 16 resting on the top surface 30b of an IOL 30. Feet 16 do not clip onto IOL 30. In some embodiments, feet 16 have a bottom surface 16a that is generally planar with posterior surface 20 of optic portion 14 as shown in FIGS. 3-4 and 6. In some embodiments, as illustrated in FIG. 7, feet 16 extend downward or posterior to posterior surface 20, creating an open gap 36 between posterior surface 20 and bottom surface 16a of feet 16. This arrangement spaces the posterior surface of the optic portion above IOL 30 to minimize or prevent an inter-lenticular membrane forming.

Figure 5:
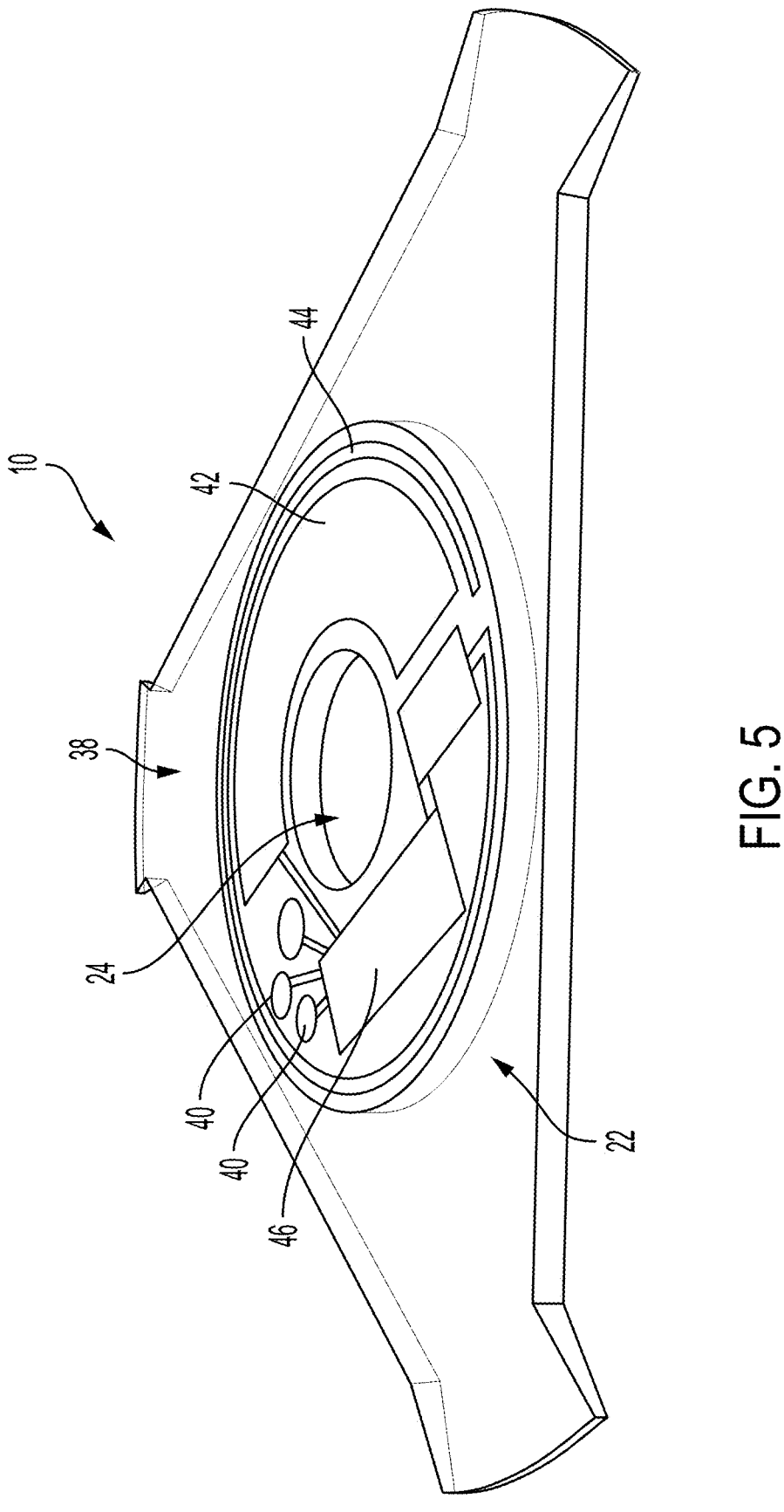
FIG. 5 is a top perspective view of an exemplary pinhole intraocular onlay with electronics mounted in the annular mask.

FIG. 5 illustrates an exemplary pinhole intraocular onlay 10 having electronics 38 located with annular mask 22. Electronics 38 includes one or more sensors 40 to measure one or more biologic conditions. For example, and without limitation, the biologic conditions include blood glucose and intraocular pressure. One or more sensors may emit high-frequency radio-waves that penetrate the eye and provides data on the characteristics of blood. Electronics 38 may further include an electric power source 42 such as a solar panel, an antenna 44, and a processor 46.

Although relative terms such as "outer," "inner," "upper," "lower," and similar terms have been used herein to describe a spatial relationship of one element to another, it is understood that these terms are intended to encompass different orientations of the various elements and components in addition to the orientation depicted in the figures. Furthermore, as used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements. The terms "substantially," "approximately," "generally," and "about" are defined as largely but not necessarily wholly what is specified (and includes what is specified; e.g., substantially 90 degrees includes 90 degrees and substantially parallel includes parallel), as understood by a person of ordinary skill in the art. The extent to which the description may vary will depend on how great a change can be instituted and still have a person of ordinary skill in the art recognized the modified feature as still having the required characteristics and capabilities of the unmodified feature.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. An intraocular onlay sized and configured for positioning within a capsular bag, comprising:
a body comprising an optic portion and feet;
the optic portion comprising:
an anterior surface and a posterior surface;
an annular mask of a selected optical opacity forming a pinhole; and
a second optically transparent region exterior to the annular mask; and
the feet having a bottom surface that is coplanar with the posterior surface of the optic portion, and the feet are sized and configured in use to be positioned within a capsular bag and to rest with the bottom surface of the feet resting on top of an existing intraocular lens that is located in the capsular bag such that the feet are not anchored to the intraocular lens,
wherein the pinhole is an opening in the body extending through the anterior surface and the posterior surface,
wherein the feet extend radially away from the annular mask and are sized and configured to extend outside of a periphery of a lens portion of the existing intraocular lens when the bottom surface is resting on top of the existing intraocular lens,
wherein the onlay is not secured to the periphery of the lens portion of the existing intraocular lens, allowing the onlay to be moved and the pinhole to be aligned with a visual axis of the eye when the existing intraocular lens is decentered.

2. The intraocular onlay of claim 1, wherein the annular mask is less than 100% light-blocking.

3. The intraocular onlay of claim 1, further comprising electronics located with the annular mask, the electronics comprising:
a sensor to measure a biologic condition; and
a transmitter coupled to the sensor to communicate the biologic condition measured by the sensor.

4. The intraocular onlay of claim 3, wherein the biologic condition comprises intraocular pressure.

5. The intraocular onlay of claim 3, wherein the biologic condition comprises blood glucose.

6. An apparatus for addressing pseudophakic presbyopia, the apparatus comprising:
an intraocular lens (IOL) with a lens portion having a periphery and haptics sized and configured to be positioned in a capsular bag of an eye; and
an onlay comprising a body having feet and an optic portion, the optic portion comprising:
an anterior surface and a posterior surface;
an annular mask of a selected optical opacity forming a pinhole; and
a second optically transparent region exterior to the annular mask;
wherein the feet have a bottom surface that is planar and the onlay is sized and configured to be positioned with the bottom surface of the feet resting on top of the lens portion of the IOL and under a capsulorhexis edge of the capsular bag with the pinhole aligned on a visual axis of the eye,
wherein the bottom surface of the feet is coplanar with the posterior surface of the optic portion and the feet are not secured to the IOL in the capsular bag,
wherein the feet extend radially away from the annular mask and are sized and configured to extend outside of the periphery of the lens portion of the IOL when the bottom surface is resting on top of the lens portion of the IOL,
wherein the onlay is not secured to the periphery of the lens portion of the IOL, allowing the onlay to be moved and the pinhole to be aligned with the visual axis of the eye when the IOL is decentered.

7. The apparatus of claim 6, wherein the pinhole is an opening in the body extending through the anterior surface and the posterior surface.

8. An intraocular onlay sized and configured for positioning within a capsular bag, comprising:
a body comprising an optic portion and feet;
the optic portion comprising:
an anterior surface and a posterior surface;
an annular mask of a selected optical opacity forming a pinhole; and
a second optically transparent region exterior to the annular mask; and
the feet having a bottom surface that is planar and separated from the posterior surface by a gap, wherein the feet are sized and configured in use to be positioned within a capsular bag and to rest with the bottom surface of the feet resting on top of an existing intraocular lens that is located in the capsular bag whereby the posterior surface is separated from the intraocular lens by the gap, wherein the bottom surface is parallel to the posterior surface, wherein the feet extend radially away from the annular mask and are sized and configured to extend outside of a periphery of a lens portion of the existing intraocular lens when the bottom surface is resting on top of the existing intraocular lens, wherein the onlay is not secured to the periphery of the lens portion of the existing intraocular lens, allowing the onlay to be moved and the pinhole to be aligned with a visual axis of the eye when the existing intraocular lens is decentered.

9. The intraocular onlay of claim 8, further comprising electronics located with the annular mask, the electronics comprising:

a sensor to measure a biologic condition; and a transmitter coupled to the sensor to communicate the biologic condition measured by the sensor.

\* \* \* \* \*